United States Patent [19]

Spivack et al.

[11] 4,038,249
[45] July 26, 1977

[54] METAL SALTS OF BENZOYLOXYBENZOATES AND COMPOSITIONS STABILIZED THEREWITH

[75] Inventors: John D. Spivack, Spring Valley; John J. Luzzi, Carmel, both of N.Y.

[73] Assignee: Ciba-Geigy Corporation, Ardsley, N.Y.

[21] Appl. No.: 600,235

[22] Filed: July 30, 1975

Related U.S. Application Data

[62] Division of Ser. No. 360,290, May 14, 1973, Pat. No. 3,920,712.

[51] Int. Cl.² .................. C08K 5/56; C08K 5/53; C08K 5/09; C07F 15/04; C07F 9/48; C07F 9/46; C07F 15/00
[52] U.S. Cl. .................. 260/45.75 R; 260/45.75 T; 260/45.75 C; 260/45.75 N; 260/45.75 W; 260/45.85 B; 260/429.7; 260/438.1; 260/45.8 N; 260/439 R
[58] Field of Search ............ 260/45.75, 45.85 B, 260/439, 429.7, 438.1, 435

[56] References Cited

U.S. PATENT DOCUMENTS 3,367,870  2/1968  Spivack ............... 260/45.95 D

*Primary Examiner* — V. P. Hoke
*Attorney, Agent, or Firm* — Nestor W. Shust; Charles W. Vanecek

[57] ABSTRACT

Metal salts of benzoyloxybenzoates having the formula

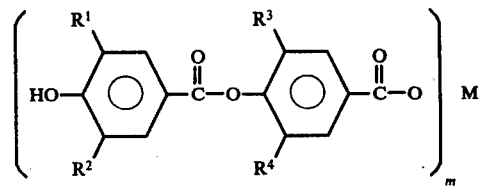

wherein
$R^1$ and $R^2$ are lower alkyl or cycloalkyl,
$R^3$ and $R^4$ are hydrogen, lower alkyl or cycloalkyl,
M is a metal or an alkylmetal moiety, and
$m$ is an integer from 1 to 4, are useful as stabilizers of organic materials such as polyolefins.

12 Claims, No Drawings

METAL SALTS OF BENZOYLOXYBENZOATES AND COMPOSITIONS STABILIZED THEREWITH

This is a divisional of application Ser. No. 360,290 filed on May 14, 1973, now U.S. Pat. No. 3,920,712.

BACKGROUND OF THE INVENTION

Polymeric materials have one important deficiency which must be overcome before they can be used in various commercial applications. This deficiency is the susceptibility to oxidative and actinic degradation. Many varieties of compounds have been known to be useful as stabilizers of various polymers, but all of them have certain deficiencies which limits the usefulness of such stabilizers. Thus, one class of stabilizers disclosed in the prior art that is related to the compounds of this invention is hindered hydroxybenzoates disclosed in U.S. Pat. Nos. 3,029,276; 3,112,338; 3,206,431 and 3,502,613. British Pat. No. 991,591 also discloses nickel salts of hindered phenolic benzoates.

The compounds of this invention are metal salts of benzoyloxybenzoates. Thus, they are totally different from the various esters of 3,5-dialkyl-4-hydroxybenzoic acids disclosed in the above noted patents and also substantially different from the metal salts of hindered phenolic benzoates. One important difference in the properties between the prior art compounds discussed above and the metal salts of benzoyloxybenzoates of this invention is the improved thermal stability of the instant compounds. This is a very important feature because the polymer substrates which are stabilized with such compounds are subjected to high temperature processing during the various manufacturing stages. Compounds which are not thermally stable will decompose during processing which will result in decreased stabilization effectiveness during the life of the polymer and also may introduce discoloration.

The compounds of this invention also have better gas fading properties and have better water and organic solvent extraction resistance than the prior art compounds.

Furthermore, the compounds of this invention have better color stability to artificial light than the prior art compounds.

DETAILED DISCLOSURE

This invention relates to hindered benzoyloxybenzoate compounds and organic compositions stabilized therewith. More specifically, these compounds are useful as stabilizers of organic materials which are subject to thermal, oxidative and ultraviolet light degradation. The novel benzoyloxybenzoate compounds can be represented by the formula

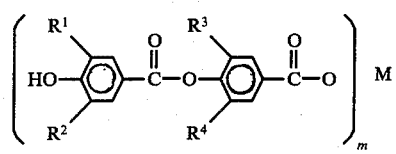

wherein
 $R^1$ and $R^2$ are (lower)alkyl or (lower)cycloalkyl groups,
 $R^3$ and $R^4$ are hydrogen, (lower)alkyl or (lower)cycloalkyl groups,
 M is a metal or an alkylmetal moiety, and
 $m$ is an integer from 1 to 4.

Each of the groups $R^1$, $R^2$, $R^3$ and $R^4$ can be the same or different (lower)alkyl groups having from 1 to 8 carbon atoms, namely, methyl, ethyl, n-propyl, isopropyl, n-butyl, sec-butyl, tert-butyl, sec-amyl, tert-amyl, n-hexyl, sec-hexyl, sec-octyl, tert-octyl and the like. These groups can also be (lower)cycloalkyl groups having 5 to 8 carbon atoms such as cyclopentyl, cyclohexyl or cyclooctyl groups. $R^3$ and $R^4$ can also be hydrogen.

Although groups $R^1$, $R^2$, $R^3$ and $R^4$ can be any (lower)alkyl groups stated above, it is preferable that $R^1$ and $R^2$ groups be secondary or tertiary and especially tertiary alkyl groups having from 4 to 8 carbon atoms. Tertiary butyl groups are found to be very effective. The above formula indicates that $R^3$ and $R^4$ can be substituted on any of the four open positions in the benzene ring but preferably both groups are ortho to the benzoic acid moiety. The group M is either a metal having 1 to 4 valences or an alkyltin group wherein part of tin's valence is satisfied by an alkyl groups having up to 8 carbon atoms. The metals which form the salts are sodium, potassium, cadmium, zinc, barium, nickel, aluminum, tin, chromium, cobalt, manganese, iron, copper, titanium and vanadium. Of the metals listed above, those having the valency of 2 to 4 are preferred. The most preferred metals are aluminum and the transitional metals having a valency of 2, such as nickel, cobalt, copper, chromium, manganese, tin and zinc.

Following are illustrative examples of the compounds of this invention:
 sodium-[4-(3,5-di-t-butyl-4-hydroxy-benzoyloxy)-3,5-di-t-butylbenzoate]
 potassium-[4-(3,5-diisopropyl-4-hydroxybenzoyloxy)-3-t-butylbenzoate]
 nickel-bis-[4-(3,5-di-t-butyl-4-hydroxybenzoyloxy)-3,5-di-t-butylbenzoate]
 cupric-bis-[4-(3,5-di-t-butyl-4-hydroxybenzoyloxy)-3,5-di-t-butylbenzoate]
 zinc-bis-[4-(3,5-di-t-butyl-4-hydroxybenzoyloxy)-3,5-di-t-butylbenzoate]
 ferrous-bis-[4-(3,5-diethyl-4-hydroxybenzoyloxy)-3,5-dimethylbenzoate]
 manganese-bis-[4-(3,5-di-t-butyl-4-hydroxybenzoyloxy)-3,5-dimethylbenzoate]
 cobalt-bis-[4-(3,5-di-tert.butyl-4-hydroxybenzoyloxy)-3,5-diisopropylbenzoate]
 ferric-tris-[4-(3,5-di-t-butyl-4-hydroxybenzoyloxy)-3,5-di-t-butylbenzoate]
 nickel-bis-[4-(3,5-diisopropyl-4-hydroxybenzoyloxy)-3,5-diisopropylbenzoate]
 di-n-butyltin-bis-[4-(3,5-di-t-butyl-4-hydroxybenzoyloxy)-3,5-di-t-butylbenzoate]
 cadmium-bis-[4-(3,5-di-t-octyl-4-hydroxybenzoyloxy)-3,5-di-t-octylbenzoate]
 cupric-bis-[4-(3,5-di-t-butyl-4-hydroxybenzoyloxy)-3,5-di-t-butylbenzoate]
 nickel-bis-[4-(3,5-di-t-butyl-4-hydroxybenzoyloxy)-benzoate]
 di-n-octyltin-bis-[4-(3,5-di-t-butyl-4-hydroxybenzoyloxy)-3,5-di-t-octylbenzoate]
 manganese-bis-[4-(3,5-di-t-butyl-4-hydroxybenzoyloxyl)-benzoate]
 nickel-bis-[4-(3,5-di-t-butyl-4-hydroxybenzoyloxy)-3-t-butylbenzoate]
 cupric-bis-[4-(3,5-di-t-butyl-4-hydroxybenzoyloxy)-3-t-butylbenzoate]

nickel-bis-[4-(3,5-di-t-butyl-4-hydroxybenzoyloxy)-3,5-dimethylbenzoate]

nickel-bis-{4-(3,5-[1,1,3,3-tetramethylbutyl]-4-hydroxybenzoyloxy)-3,5-[1,1,3,3-tetramethylbutyl]benzoate} cupric-bis-[4-(3,5-dicyclooctyl-4-hydroxybenzoyloxy)-3,5-dicyclooctylbenzoate]

manganese-bis-[4-(3,5-dicyclopentyl-4-hydroxybenzoyloxy)-3-cyclopentylbenzoate]

chromium-tris-[4-(3,5-di-t-butyl-4-hydroxybenzoyloxy)-3,5-di-t-butylbenzoate]

aluminum-tris-[4-(3,5-di-t-octyl-4-hydroxybenzoyloxy)-3,5-di-t-octylbenzoate]

molybdenum-tetrakis-[4-(3,5-di-t-butyl-4-hydroxybenzoyloxy)-3,6-dimethylbenzoate]

vanadium-tris-[4-(3,5-di-t-butyl-4-hydroxybenzoyloxy)-3,5-di-t-butylbenzoate]

titanium-tetrakis-[4-(3,5-di-t-butyl-4-hydroxybenzoyloxy)-3,5-di-t-butylbenzoate]

tin-tetrakis-[4-(3,5-di-t-butyl-4-hydroxybenzoyloxy]-3,5-dimethylbenzoate

Another embodiment of this invention is a polymeric metal benzoyloxybenzoate having the repeating unit

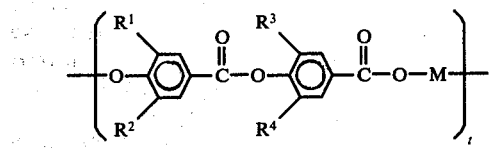

II wherein the symbols $R^1$, $R^2$, $R^3$, $R^4$ and M are as previously defined and it is up to about 50 and preferably up to about 25.

The compounds of this invention when $R^1$ and $R^2$ are different from $R^3$ and $R^4$ can be prepared by reacting a hindered phenolic acid chloride such as 3,5-di-t-butyl-4-hydroxybenzoylchloride with an appropriate alkyl substituted benzoate at a temperature of from about 50° to 200° C followed by hydrolysis to the alkali metal salt and conversion to the appropriate metal salt as appropriate. Compounds where $R^1$ and $R^2$ are the same as $R^3$ and $R^4$ can be prepared by reacting two moles of a dialkyl substituted hydroxybenzoyl halide with one mole of a base to yield an intermediate compound which is (di-alkyl substituted hydroxybenzoyloxy)dialkyl benzoyl halide. The basic materials which can be employed are trialkyl amines such as triethyl amine, tripropyl amine, triisopropyl amine, tributyl amine, triamyl amine, sodium or potassium hydroxide, sodium or potassium carbonates or other similar proton acceptors. The intermediate benzoyloxybenzoyl halide is then hydrolyzed with an alkali such as hydroxide to yield the corresponding alkali metal salt of benzoyloxybenzoic acid and converted to the metal (m) salt in known fashion. Both syntheses of the intermediate benzoyloxybenzoic acid mentioned above can be carried out in a non-reactive solvent such as a hydro-carbon as for example, hexane, cyclohexane, heptane, non-reactive chlorinated hydrocarbon, mineral oil, and preferably benzene or toluene. The final metal benzoyloxybenzoate product is prepared by reacting the acid with a metal halide, such as nickel chloride, under alkaline conditions. This reaction can be carried out advantageously in water or in a polar solvent in general, such as for example, methanol, ethanol, isopropanol or mixtures thereof or other similar solvents. Water may also be used and in this case the salt of M precipitates being water insoluble.

In the above general formula I, mineral salts may also be formed where the valence of the metal ion M is satisfied by both the benzoyloxybenzoate anions as well as other anions such as the amine of alkyl and dialkyl-phosphoric acid, alkyl phosphonate, aryl-phosphonate, acetate, laurate, octanoate, stearate, hydroxyphenyl carboxylate, benzoate, substituted benzoate, hydroxyalkylbenzyl phosphonate, hydroxyalkylbenzyl phosphinate and the like. Thus, another embodiment of this invention are mixed hydroxyalkylbenzyl phosphonate and phosphinate mixed salts with the benzoyloxybenzoate anions exemplified by the following generic formula

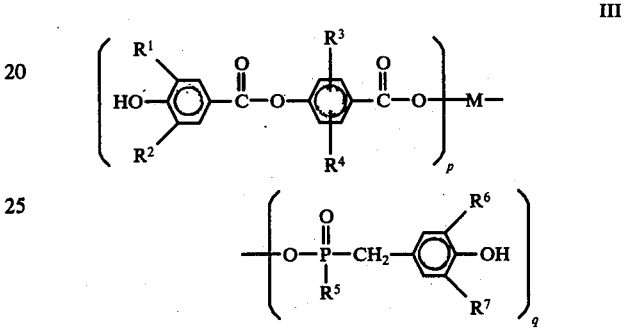

III wherein $R^1$, $R^2$, $R^3$, $R^4$ and M are as defined above, $R^5$ is lower alkoxy, phenyl, and lower alkyl, $R^6$ and $R^7$ are lower alkyl, preferably t-butyl and $p$ and $q$ are integers the sum of which equals the valence of M.

In addition, the coordination numbers of the metal may be satisified by polar ligands such as water, alcohol, glycols, and diols, triols, tetraols, pentols, hexitols, as well as ammonia, amines, amino-alcohols, tertiary aminophosphines and the like.

To further exemplify this invention, there are presented below the following examples.

EXAMPLE 1

Preparation of 4-(3,5-di-t-butyl-4-hydroxybenzoyloxy)-3,5-di-t-butyl-benzoyl chloride To 425 ml of a toluene solution containing 107.2 grams of 3,5-di-t-butyl-4-hydroxybenzoyl chloride (0.40 moles) cooled to 10° C was added 24.4 grams (0.24 moles) of triethylamine over a period of 20 minutes at 10° to 15° C. The turbid reaction mixture was maintained at room temperature for about 19 hours and then heated at 80° C for 1 hour. The precipitate was removed by filtration and washed with a little toluene. The clear filtrate was concentrated in vacuo at 40° to 50° C at 20 mm. Hg. pressure and kept at this same temperature for 45 minutes at 20 mm. Hg. pressure to yield 105 grams of residue. The residue was triturated with 200 ml. of warm petroleum ether, and the slurry cooled. The white crystals were filtered yielding 70 grams of the product. After recrystallization from heptane and acetonitrile and drying at 95° C for 5 hours at 0.1 mm Hg. pressure the melting point of the product was 210°–213° C.

EXAMPLE 2

Preparation of
4-(3,5-di-tert-butyl-4-hydroxybenzoyloxy)-3,5-di-tert-butylbenzoic acid 25.2 g of triethylamine was added dropwise to 505 ml. of 0.99 molar toluene solution of 3,5-di-t-butyl-4-hydroxybenzoyl chloride at 10° to 15° C over a period of 15 minutes in a nitrogen atmosphere. The reaction was allowed to stir for an additional 2¼ hours at room temperature (25° C). The precipitated triethylamine hydrochloride was filtered and washed with a little toluene.

450 ml of 2N sodium hydroxide were added to the toluene filtrate at room temperature and gradually heated to reflux. The reaction was heated at reflux for 4½ hours. The reaction mixture was cooled to 0° to 5° C by an ice-water bath whereupon a thick precipitate formed consisting of the intermediate sodium 4-(3,5-di-tert-butyl-4-hydroxybenzoyloxy)-3,5-di-tert-butylbenzoate. 70 ml of concentrated aqueous hydrochloric acid was gradually added dropwise with cooling at 30° C. 150 ml of ether was added with stirring to the reaction mixture at 20° to 25° C. The aqueous phase was separated and the organic phase washed with two 100 ml portions of water. The separated organic phase was then dried over anhydrous sodium sulfate. The residue was isolated from the organic phase by evaporation of the solvent initially at about 20 mm Hg. pressure and finally at 0.5 mm Hg.

The glassy residue was ground in a mortar and then triturated with stirring at reflux with a 150 ml portion of petroleum ether in a 3-neck flask. The slurry was then cooled to room temperature, the solid isolated by filtration and triturated once again. The petroleum ether filtrate from the second trituration was colorless. After drying in the vacuum oven overnight at 40° C at 1 mm. Hg. pressure, the product was isolated as a white powder. The product melts at about 301° to 306° C, the melting range depends on the heating rate.

EXAMPLE 3

Nickel-bis-[4-(3,5-di-tert-butyl-4-hydroxybenzoyloxy)-3,5-di-tert-butylbenzoate]

To 4.92 g of 4-(3,5-di-tert-butyl-4-hydroxybenzoyloxy)-3,5-di-tert-butylbenzoic acid (0.01 moles) was added 10 ml. of 1.00 N methanolic potassium hydroxide at 25° C in a nitrogen atmosphere resulting in a clear light-yellowish solution. 1.19 g of nickel chloride hexahydrate dissolved in 10 ml of hot methanol was added dropwise at 26° C over a period of 5 minutes. The reaction mixtur was stirred at 50° to 60° C for an additional two hours. The resulting fine precipitate was filtered by suction and washed with isopropanol and ether. The green aqueous filtrate was concentrated to dryness by distillatin of the solvent under vacuum and the residue dissolved in 100 ml of hot benzene. The benzene solution was then concentrated to dryness at 0.1 mm Hg. at 50° to 60° C. After grinding a light-yellow powder was obtained melting at 280°–290° C.

This product was recrystallized from ethanol. After drying at 27° C for 54 hours at 0.1 mm Hg. analysis showed that the green crystals (melting point 250°–260° C) contain 2 moles of ethanol of crystallization. When the nickel salt was prepared from a water dispersion of the sodium salt of Example 2, the nickel salt described above was isolated as the dihydrate melting at about 300° to 310° C.

EXAMPLE 4

Nickel-bis-[4-(3,5-di-tert-butyl-4-hydroxybenzoyloxy)-3,5-di-tert-butylbenzoate]

a. 4-(3,5-di-tert-butyl-4-hydroxybenzoyloxy)-3,5-di-tert-butylbenzoic acid

Triethylamine (25.2 g) was added dropwise to 505 ml of 0.99 M toluene solution of 3,5-di-tert-butyl-4-hydroxybenzoyl chloride at 10° to 15° C over a period of 15 minutes in a nitrogen atmosphere. The reaction was allowed to stir for an additional 2¼ hours at room temperature (25° C). The precipitate was filtered, washed with a little toluene and dried at 60° C. at 100 mm. Hg. pressure overnight recovering the precipitate triethylamine hydrochloride.

To the toluene filtrate were added at room temperature 450 ml of 2N sodium hydroxide and the reaction mixture was gradually heated to reflux to minimize initial foaming. The reaction was heated at reflux for 4½ hours. The reaction mixture was cooled to 0° to 5° C. by an ice-water bath whereupon a thick precipitate formed, consisting of the intermediate sodium 4-(3,5-di-tert-butyl-4-hydroxybenzoyloxy)-3,5-di-tert-butyl-benzoate. This compound was a white solid which did not melt at 300° C. 70 ml of concentrated aqueous hydrochloric acid was gradually added dropwise with cooling at 30° C. 150 ml of ether were added with stirring to the reaction mixture at 20° to 25° C. The aqueous phase was separated and the organic phase washed with two 100 ml portions of water. The separated organic phase was then dried over anhydrous sodium sulfate. The residue was isolated from the organic phase by evaporation of the solvent initially at about 20 mm. Hg. pressure and finally at 0.5 mm. Hg. The glassy residue was ground and then triturated with stirring at reflux with a 150 ml. portion of petroleum ether in a 3-neck flask. The slurry was then cooled to room temperature, the solid isolated by filtration and triturated once again. The white crystalline precipitate from the second trituration was dried in the vacuum oven overnight at 40° C at 1 mm. Hg. pressure. The product was isolated as a white powder weighing 102 grams (84.5% yield). The product melted at about 301° to 306° C, the melting range depending on the heating rate.

b. Nickel-bis-[4-(3,5-di-tert-butyl-4-hydroxybenzoyloxy)-3,5-di-tert-butylbenzoate]

To a 150 ml water dispersion of 24.35 grams the intermediate prepared above were added 25 ml of 2N sodium hydroxide and then stirred for 30 minutes at 50° C. A solution of 5.92 $NaCl_2.6H_2O$ in 30 ml of water was added dropwise at 45° to 50° C over a period of 15 minutes. The resulting green dispersion was stirred at 45° to 50° C for two hours and at room temperature for 3 hours. The precipitated green solid was filtered under vacuum and washed by reslurrying four times with 30 ml portions of cold water. The product was dried overnight in the vacuum dessicator over anhydrous calcium sulfate at 0.4 mm Hg. pressure. Fresh calcium sulfate was then added and drying continued for 48 hours. The resulting product weight 20 g and had a melting point of 300°–310° C.

Following procedure (a) in the above example the following benzoic acid compounds are also prepared by employing the appropriate starting materials.

4-(3,5-dimethyl-4-hydroxybenzoyloxy)-3,5-dimethylbenzoic acid 4-(3,5-di-t-butyl-4-hydroxybenzoyloxy)-3-methylbenzoic acid 4-(3,5-di-t-butyl-4-hydroxybenzoyloxy)-benzoic acid 4-(3,5-dicyclopentyl-4-hydroxybenzoyloxy)-3,5-dicyclopentylbenzoic acid.

Following procedure (b) described above, nickel, titanium, manganese, cobalt, chromium and copper salts are prepared.

EXAMPLE 5

Cupric-bis-[4-(3,5-di-tert-butyl-4-hydroxybenzoyloxy)-3,5-di-tert-butylbenzoate]

The cupric salt was made by substantially the same procedure as described in Example 4(b) by substituting cupric chloride dihydrate in place of nickel chloride. The product was isolated as a green powder having about two moles of water of crystallization in the complex and melting at 270° to 275° C.

EXAMPLE 6

Zinc-bis-[4-(3,5-di-tert-butyl-4-hydroxybenzoyloxy)-3,5-di-tert-butylbenzoate]

The zinc salt was made by substantially the same procedure as described in Example 4(b) by substituting zinc chloride in place of the nickel compound. The product was isolated as a white powder having an average of about 1.3 mole of water of crystallization in the complex and melting at about 335° to 340° C.

EXAMPLE 7

Nickel-bis-[4-(3,5-dimethyl-4-hydroxybenzoyloxy)-3,5-dimethylbenzoate]

Following the procedure of Example 4(b) except for employing 4-(3,5-dimethyl-4-hydroxybenzoyloxy)-3,5-dimethylbenzoate, the above named product is prepared.

EXAMPLE 8

Chromium-bis-[4-(3,5-dicyclohexyl-4-hydroxybenzoyloxy)-3,5-dicyclohexylbenzoate]

Following the procedure of Example 4(b) except for employing 4-(3,5-dicyclohexyl-4-hydroxybenzoyloxy)-3,5-dicyclohexylbenzoic acid and chromium chloride, the above named product is prepared.

EXAMPLE 9

Manganese-bis-[4-(3,5-di-tert-butyl-4-hydroxybenzoyloxy)-3,5-di-tert-butylbenzoate]

The manganese salt was made by substantially the same procedure as in Example 4(b) by substituting manganese chloride tetrahydrate in place of the nickel compound. The product was isolated as an off-white powder which did not melt up to a temperature of 340° C and had an average of 1.5 moles of water of crystallization in the complex.

EXAMPLE 10

Ferric-tris-[4-(3,5-di-tert-butyl-4-hydroxybenzoyloxy)-3,5-di-tert-butylbenzoate]

The ferric salt was made by substantially the same procedure as in Example 4(b) by substituting ferric chloride hexahydrate in place of the nickel compound. The product was isolated as a brown powder melting at 290° C with decomposition.

EXAMPLE 11

Aluminum-tris-[4-(3,5-di-t-butyl-4-hydroxybenzoyloxy)benzoate]

Following the procedure of Example 4(b) except for employing 4-(3,5-di-t-butyl-4-hydroxybenzoyloxy)benzoic acid and aluminum chloride, the above named product is prepared.

EXAMPLE 12

Di-n-butyltin-bis-[4-(3,5-di-t-butyl-4-hydroxybenzoyloxy)-3,5-di-tert-butylbenzoate]

4.12 grams of 4-(3,5-di-tert-butyl-4-hydroxybenzoyloxy)-3,5-di-tert-butylbenzoic acid (0.01 moles) and 1.244 grams of di-n-butyltin oxide (0.005 moles) dissolved in 100 ml of benzene were heated at reflux for 5 hours under nitrogen, while removing the water by azeotropic distillation. The slightly turbid reaction solution was clarified by filtration through filtercel and the clear filtrate concentrated by distillation under reduced pressure yielding a glassy residue. The residue was crystallized from n-heptane yielding white crystals. After drying at 85° C at 0.10 mm Hg. for 20 hours, the white crystals melted at 172°–175° C to a clear melt, but on further heating became solid and melted again at 230°–235° C.

| Analysis: | Calculated | Found |
|---|---|---|
| % C | 68.27 | 68.26 |
| % H | 8.86 | 8.10 |
| % Sn | 9.93 | 9.11 |

EXAMPLE 13

Preparation of Dipotassium salt of 4-(3,5-di-t-butyl-4-hydroxybenzoyloxy)-3,5-di-t-butylbenzoate To 9.75 grams of 4-(3,5-di-tert-butyl-4-hydroxybenzoyloxy)-3,5-di-tert-butylbenzoic acid (0.02 moles) dispersed in 20 ml of methanol was added 40 ml of 1.00 N methanolic potassium hydroxide. The clear solution was then warmed to 30° C for 10 minutes forming the dipotassium salt.

EXAMPLE 14

Polymeric nickel-[4-(3,5-di-tert-butyl-4-hydroxybenzoyloxy)-3,5-di-tert-butylbenzoate]

To a methanolic solution of the dipotassium salt of 4-(3,5-di-tert-butyl-4-hydroxybenzoyloxy)-3,5-di-tert-butylbenzoate (0.02 moles) in about 60 ml of methanol as prepared in Example 13 was added dropwise at 30° C a solution of 4.74 g of nickel chloride hexahydrate (0.02 moles). After the addition is complete, the turbid reaction mixture was heated at reflux for 5 hours. The methanol was then removed by stripping on the Rotofilm Evaporator under reduced pressures. The light green residue was then dissolved in 50 ml of hot toluene and the white insoluble potassium chloride removed by filtration. The clear green toluene filtrate was concentrated at reduced pressures and the isolated residual product kept at 50°–60° C and 0.30 mm Hg. for 3 hours yielding the product as a yellow-green powder melting at 300°–310° C. Molecular weight determination of the product indicates the number average molecular weight of the compound is 7000.

EXAMPLE 15

Preparation of triethanolamine complex of Nickel bis-4-(3,5-di-tert-butyl-4-hydroxybenzoyloxy)-3,5-di-tert-butylbenzoate 7.5 grams of triethanolamine in 100 ml of absolute ethanol are added dropwise to 52.8 grams of nickel-bis-(3,5-di-tert-butyl-4-hydroxybenzoyloxy-benzoate) dissolved in 500 ml of absolute ethanol. The reaction mixture is stirred for 15 minutes at room temperature and then heated at reflux for two hours. The solvent is removed by distillation at reduced pressure and the green residue thus obtained is dried for 20 hours at 60° C at about 0.10 mm Hg pressure.

In a similar manner compounds of the following structure are prepared:

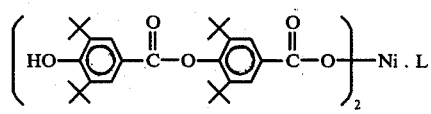

where + is tert-butyl group and L is the following:

NH(CH₂CH₂OH);     NH₂CH₂CH₂OH;
(CH₃)₂NCH₂CH₂OH;     C₄H₉N(CH₂CH₂OH)₂;
C₁₂H₂₅OCH₂CHOHCH₂OH;

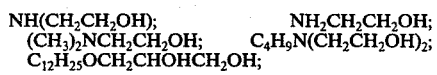

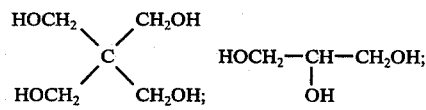

EXAMPLE 16

Preparation of O-ethyl-3,5-di-tert-butyl-4-hydroxybenzylphosphonatonickel-4-(3,5-di-tert-butyl-4-hydroxybenzoyloxy)-3,5-di-tert-butylbenzoate 23.5 grams of nickel chloride hexahydrate dissolved in 100 ml of methanol are added dropwise to a solution of 35 g sodium O-ethyl-3,5-di-tert-butyl-4-hydroxybenzyl phosphonate in 500 ml of absolute ethanol at 50° C. The precipitated sodium chloride is filtered. This solution is then added to a solution of 50.5 g of sodium 4-(3,5-di-tert-butyl-4-hydroxybenzoyloxy)-3,5-di-tert-butyl-benzoate in 500 ml ethanol at reflux. The reaction product is heated at a reflux temperature for two hours. After cooling to room temperature, the precipitated sodium chloride is filtered, the solvent is removed at reduced pressures and the residue isolated as a glass, which is ground to a powder. In a similar manner, the following compounds are obtained:

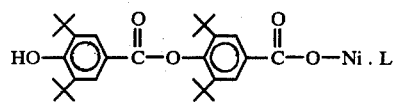

where + is tert-butyl and L is

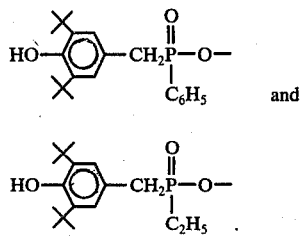

The metal salts of benzoyloxybenzoates of this invention are stabilizers of organic material normally subject to thermal, oxidative or actinic light deterioration. Materials which are thus stabilized include synthetic organic polymeric substances such as vinyl resins formed from the polymerization of vinyl halides or from the copolymerization of vinyl halides with unsaturated polymerizable compounds, e.g., vinyl esters, α,β-unsaturated ketones, α,β-unsaturated aldehydes and unsaturated hydrocarbons such as butadienes and styrene; poly-α-olefins such as polyethylene, polypropylene, polybutylene including copolymers of α-olefins; dienes such as polybutadiene, polyisoprene, and the like, including copolymers such as polyhexamethylene adipamide and polycaprolactam; polyesters such as polyethylene terephthalates; polycarbonates; polyacetals such as polyformaldehyde; polystyrene, polyethyleneoxide; and copolymers such as those of high impact polystyrene containing copolymers of butadiene and styrene and those formed by the copolymerization of acrylonitrle, butadiene and/or styrene.

Other materials which can be stabilized by the compounds of the present invention include lubricating oil of the aliphatic ester type, i.e., di(2-ethylene)-azelate, pentaerythritol tetracaproate, and the like; animal and vegetable derived ols, e.g., linseed oil, fat, tallow, lard, peanut oil, cod liver oil, castor oil, palm oil, corn oil, cottonseed oil, and the like hydrocarbon materials such as gasoline, mineral oil, fuel oil, drying oil, cutting fluids, waxes, resins, and the like, salts of fatty acids such as soaps and the like; and alkylene glycols, e.g., β-methoxyethyleneglycol, methoxytriethyleneglycol, triethyleneglycol, octaethyleneglycol, dibutyleneglycol, dipropyleneglycol and the like.

Of particular importance are polyolefins and especially polypropylene because these benzoyloxybenzoates are particularly effective as UV stabilizers in polypropylene.

In general, the stabilizers of this invention are employed from about 0.01 to about 5% by weight of the stabilized composition, although this will vary with the particular substrate and the application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, or the like into films, fibers, filaments, hollow spheres and the like. The heat stabilizing properties of these compounds advantageously stabilize the polymer against degradation during such processing at the high temperature generally encountered. The stabilizers can also be dissolved in suitable solvents and sprayed on the surface of films, fabrics, filaments or the like to provide effective stabilization.

These compounds can also be used in combination with other additives such as antioxidants, sulfur-containing esters such as distearyl-β-thiodipropionate (DSTDP), dilauryl-β-thiodipropionate (DLTDP) in an amount of from 0.01 to 2% by weight of the organic material, and the like, pourpoint depressants, corrosion and rust inhibitors, dispersing agents, demulsifiers, antifoaming agents, carbon black, accelerators and other chemicals used in rubber compounds, plasticizers, color stabilizers, di- and tri-alkyl- and -alkylphenyl-phosphites, heat stabilizers, ultraviolet light stabilizers, antiozonants, dyes, pigments, metal chelating agents, dyesites including nickel alkanoates and the like. Often combinations such as these, particularly the sulfur containing esters, the phosphites and/or the ultraviolet light stabilizers in certain applications will produce superior results to those expected when only individual components are employed.

The following formula represents co-stabilizers which are in certain instances very useful in combination with the stabilizers of this invention:

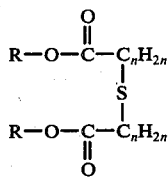

wherein R is an alkyl group having from 6 to 24 carbon atoms; and n is an integer from 1 to 6. Especially useful compounds of this type are dilauryl-β-thiodipropionate and distearyl-β-thiodipropionate. The above co-stabilizers are used in the amount of from 0.01 to 2% by weight of the organic material, and preferably from 0.1 to 1%.

Although the compounds of this invention are also effective as thermal stabilizers, if the processing of the polymer is carried out at high temperature it is advantageous to incorporate additional antioxidants.

The antioxidant compounds that can be employed are various hindered phenolic compounds which can be illustrated by the compounds listed below:
  di-n-octadecyl(3-t-butyl-4-hydroxy-5-methylbenzyl)-malonate
  2,6-di-t-butylphenol
  2,2'-methylene-bis(6-t-butyl-4-methylphenol)
  2,6-di-t-butylhydroquinone
  octadecyl-(3,5-di-t-butyl-4-hydroxybenzylthio)acetate
  1,1,3-tris(3-t-butyl-6-methyl-4-hydroxyphenyl)butane
  1,4-bis(3,5-di-t-butyl-4-hydroxybenzyl)-2,3,5,6-tetramethylbenzene
  2,4-bis-(3,5-di-t-butyl-4-hydroxyphenoxy)-6-(n-octylthio)-1,3,5-triazine
  2,4-bis-(4-hydroxy-3,5-di-t-butylphenoxy)-6-(n-octylthioethylthio)-1,3,5-triazine
  2,4-bis-(n-octylthio)-6-(3,5-di-t-butyl-4-hydroxyanilino)-1,3,5-triazine
  2,4,6-tris-(4-hydroxy-3,5-di-t-butylphenoxy)-1,3,5-triazine
  n-octadecyl β-(3,5-di-t-butyl-4-hydroxyphenyl)propionate
  2-(n-octylthio)ethyl-3,5-di-t-butyl-4-hydroxybenzoate
  stearamido N,N-bis-[ethylene 3-(3,5-di-t-butyl-4-hydroxyphenyl)propionate]
  1,2-propylene glycol bis-[3-(3,5-di-t-butyl-4-hydroxyphenyl)propionate]
  pentaerythritol tetrakis-[3-(3,5-di-t-butyl-4-hydroxyphenyl)propionate]
  dioctadecyl-3,5-di-t-butyl-4-hydroxybenzylphosphonate
  di-n-octadecyl-1-(3,5-di-t-butyl-4-hydroxyphenyl)-ethanephosphonate The above antioxidants have been listed only for the purpose of illustration and it is important to note that any other antioxidant can be employed producing similar improved results. The above exemplified antioxidants are disclosed in greater detail in the following patents: Netherlands Pat. No. 67/1119, issued Feb. 19, 1968; Netherlands Pat. No. 68/03498 issued Sept. 18, 1968; U.S. Pat. Nos. 3,255,191; 3,330,859; 3,281,505; 3,285,855; 3,364,250; 3,368,997 and 3,357,944.

To further illustrate the present invention additional examples are presented without introducing any limitations to the description of the invention.

Outdoor Light Exposure Test

15 Denier Oriented Monofilaments

The additives are solvent blended (e.g., methylene chloride) with powdered polypropylene (Hercules Profax 6501). The solvent is then removed at room temperature in a vacuum oven with a slight air bleed. The dry mixture is melt-extruded at 450° F and pelletized. The pellets are reextruded through a monofilament die, melt spun and hot oriented 4:1 by means of a set of cold and hot Godet rolls to give 15 denier (nominal) monofilaments.

The test results reported in Examples of Table I show the percentage of retention of the original tenacity by a fiber after having been exposed to the indicated number of Kilolangleys (Kly) of Florida exposure. A Langley is a measure of energy absorbed by the fiber.

Table I shows the results of the above described outdoor test indicating amounts of the additives present. Thus, in the Additives column is given the percentage of the compound prepared in the indicated Example, which is present in the polypropylene composition in addition to the additives present in the base formulation. The remaining two columns show the number of Kilolangleys of exposure in Florida at the indicated percentage of retention of the original tenacity to which the fibers have been subjected.

TABLE I

Outdoor Exposure of 15 Denier Polypropylene Monofilaments in Florida

Base Formulation: 0.2% Antioxidant*
0.1% Calcium Stearate

| Ex. No. | Additive | Kilolangleys to 30% Retention of Tenacity | Kilolangleys to 50% Retention of Tenacity |
|---|---|---|---|
| 17 | Base Formulation | 41 | 36 |
| 18 | 0.25% of Compound of Ex. 3 | 66 | 56 |
| 19 | 0.50% of Compound of Ex. 3 | 108 | 76 |
| 20 | 0.75% of Compound of Ex. 3 | >120 | 123 |
| 21 | 0.25% of Compound of Ex. 3 0.25% UV Stabilizer** | 79 | 74 |

*The Antioxidant is dioctadecyl 3,5-di-t-butyl-4-hydroxybenzylphoshponate.
**UV Stabilizer is 2-(2'-hydroxy-3',5'-di-t-butylphenyl)-5-chloro-1,2,3-benztriazole.

Proportionately good stabilization is obtained when in the compositions of Table I the compounds of this invention are present in the concentrations of 0.1% and 1%.

Artificial Light Exposure Test

Deterioration of most polymers caused by ultraviolet light is so slow at ambient temperatures even in the absence of stabilizers, that testing of the effects of stabilizers generally must be conducted either at higher temperatures or in an accelerated artificial light exposure device in order to yield results in a convenient period of time. The test conducted on polymers using an artificial light exposure device is described below:

a. Sample Preparation 5 mil Film — Unstabilized polypropylene Powder (Hercules Profax 6501) is thoroughly blended with the indicated amounts of additives. The blended material is then milled on a two roll mill for 5 minutes at 182° C. The milled sheet is then compression molded at 220° C into 5 mil thick film under a pressure of 175 psi and water cooled in the press.

b. Testing Method

This test is conducted in a FS/BL unit, basically of the American Cyanamid design, which consists of 40 tubes of alternating fluorescent sun lamps and black lights (20 of each). The 5 mil sample film are mounted on 3 × 2 inch IR card holders with ¼ × 1 inch windows and are placed on a rotating drum 2 inches from the bulbs in the FS/BL unit. The time in hours is noted for the development of 0.5 carbonyl absorbance units as determined on an Infrared Spectophotometer. The development of carbonyl functional groups in the polymer is proportional to the amount of degradation caused by the ultraviolet light exposure.

The test results reported below were obtained according to the procedures described above. The amounts of the additives are expressed in weight percent based on the weight of the polymer.

TABLE II

| Ex. No. | Formulation* | Hours to Failure |
| --- | --- | --- |
| 22 | 0.5% Compound of Ex. 5 | 635 |
| 23 | 0.5% Compound of Ex. 6 | 515 |
| 24 | 0.5% Compound of Ex. 9 | 515 |
| 25 | 0.5% Compound of Ex. 10 | 465 |
| 26 | 0.5% Compound of Ex. 12 | 520 |
| 27 | 0.5% Compound of Ex. 14 | 685 |
| 28 | Control | 195 |

*Each sample tested and the control contains 0.2% of di-n-octadecyl(3,5-di-t-butyl-4-hydroxybenzyl)phosphonate which is an antioxidant that prevents oxidative degradation of polypropylene.

Similar results are obtained when the compounds of Examples 15 and 16 are employed.

EXAMPLE 29

Pellets (500 g) of unstabilized nylon-6,6 (Zytel 101, DuPont) are placed in a Kitchen Aid Mixer. With mixing, a solution of 0.5% (based on the weight of nylon) of manganese-bis-[4-(3,5-di-t-butyl-4-hydroxybenzoyloxy)-3-methylbenzoate] in 20 ml of methylene chloride is added slowly. Sodium hypophosphite (0.5 gm 0.1%) is dissolved in 20 ml of water and added slowly with mixing to the nylon pellets after the antioxidant solution has been added and most of the methylene chloride has evaporated. The stabilized pellets are dried at 80° C at <1 mm for 4 hours.

The polyamide formulation is extruded at 600° F through a ¼ inch die into a rod which is water cooled and chopped into pellets. A ⅜ inch Brabender extruder, equipped with a nylon screw, is used. The pellets are dried at 80° C at <1 mm for 4 hours.

The dried pellets are reextruded into 5 mil (nominal) monofilament fiber which is subsequently oriented (4:1). The oriented fibers are exposed to outdoor weathering (direct and under glass) and tensile measurements are made periodically. The sample is considered to have failed when it loses 50% of its original tenacity. The sample stabilized with the above noted benzoate retained tensile strength for a much longer period than the unstabilized sample.

EXAMPLE 30

Unstabilized high impact polystyrene resin is dry blended with 0.01% by weight of the resin of zinc-bis-[4-(3,5-di-t-butyl-4-hydroxybenzoyloxy)-3,5-di-t-butylbenzoate]. The resin is then extrusion compounded on a 1 inch 24/1=L/D extruder, melt temperature 500° F and then pressed for 7 minutes at a temperature of 163° C and a pressure of 2000 psi into a sheet of uniform thickness of 100 mil. The sheets are then cut into plaques of 2 × 2 inch. The plaques are then exposed to a FS/BL exposure device and color measurements made periodically using a Hunter Color Difference Meter Model D25. The polystyrene samples stabilized with the above benzoate developed the undesirable yellow discoloration substantially later after such discoloration occurred in the unstabilized samples.

EXAMPLE 31

Unstabilized linear polyethylene is solvent blended in methylene chloride with 0.5% by weight of the substrate of cupric-bis-[4-(3,5-di-t-butyl-4-hydroxybenzoyloxy)-3,5-di-t-butylbenzoate] and then vacuum dried. The resin is then extruded at 450° F as described in Example 30. Thereafter, the test procedure of Example 30 is followed and the light stability of the samples determined. Polyethylene stabilized with the above benzoate is found to be much more stale than the unstabilized polyethylene or the polyethylene stabilized only with an antioxidant.

Similarly, good stabilization is obtained with nickel-bis-[4-(3,5-dimethyl-4-hydroxybenzoyloxy)-3,5-dimethylbenzoate] and chromium-bis-[4-(3,5-dicyclohexyl-4-hydroxybenzoyloxy)-3,5-dicyclohexylbenzoate].

EXAMPLE 32

A quantity of SBR emulsion containing 100 g of rubber (500 ml of 20% SBR obtained from Texas U.S., Synpol 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber is isolated by filtration through cheese cloth, rinsed with distilled water. After three subsequent washings with fresh distilled water, the coagulated rubber is dried, first at 25 mm Hg and finally to constant weight under high vacuum (<1 mm) at 40°–45° C.

The dried rubber (25 g) is heated under nitrogen at 125° C in a Brabender mixer and to this is added with mixing 0.5% of ferric-tris-[4-(3,5-di-t-butyl-4-hydroxybenzoyloxy)-3,5-di-t-butylbenzoate]. The composition is mixed for 5 minutes after which it is cooled and compression molded at 125° C into 5 × 0.025 inch plaques.

The plaques are exposed to a xenon arc weatherometer and the color measurement (L-b) is made after 45, 125 and 290 hours. The samples stabilized with the above benzoate is found to be much more light stable than the unstabilized samples. The expression L-b is a commonly used formula for expressing yellowness of a plaque in the Hunter color system L is a measure of the whiteness of a sample and b is an indication of the blue-yellow hue of the sample.

EXAMPLE 33

To 50 g of polyacetal resin containing 0.1% of an acid scavenger, dicyandiamide, is added 0.2% by weight of di-n-butyltin-bis-[4-(3,5-di-t-butyl-4-hydroxybenzoyloxy)-3,5-di-t-butylbenzoate], and milled for 7 minutes at 200° C in a Brabender Plasti-recorder. The milled formulation is subsequently pressed into a 40 mil sheet at 215° C at 350 psi for 90 seconds then cooled quickly in a cold press at 350 psi. The stabilized sheets are then remolded for 2 minutes at contact pressure and for 3 minutes at 300 psi at 215° C to give plaques 1½ × 2¼ inch × 125 mil. Thereafter, the testing procedure of Example 13 is followed to determine the light stability of the samples. The stabilized samples are found to be much more stable then the unstabilized samples.

EXAMPLE 34

Unstabilized thoroughly dried polyethylene terephthalate chips are dry blended with 1.0% of titanium-tetrakis-[4-(3,5-di-t-butyl-4-hydroxybenzoyloxy)-3,5-di-t-butylbenzoate]. 60/10 denier multifilament is melt spun at a melt temperature of 290° C. The oriented fiber is wound on white cards and exposed in a Xenon Arc Fadeometer. Color measurements are made periodically with a Hunter Color Difference Meter Model D25. The stabilized samples are found to be much more light stable than the unstabilized samples.

What is claimed is:

1. A benzoyloxybenzoate having the formula

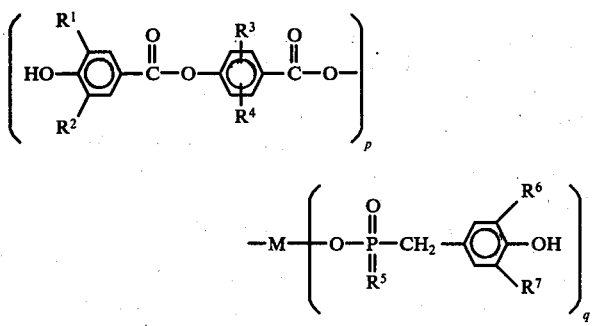

wherein
$R^1$ and $R^2$ are (lower)alkyl or (lower)cycloalkyl groups,
$R^3$ and $R^4$ are hydrogen, (lower)alkyl or (lower)cycloalkyl,
$R^5$ is (lower)alkyl, (lower)alkyloxy or phenyl,
$R^6$ and $R^7$ are (lower)alkyl,
M is a metal having a valency of 1 to 4, and $p$ and $q$ are integers, the sum of which equal the valency of M provided that neither $p$ nor $q$ is equal to $o$.

2. Compounds according to claim 1 wherein $R^1$, $R^2$, $R^3$, $R^4$, $R^6$ and $R^7$ are tert-butyl groups, M is nickel, $p$ is 1 and $q$ is 1.

3. A composition of matter stabilized against degradation which comprises an organic material subject to oxidative and ultraviolet light degradation and a benzoyloxybenzoate having the formula

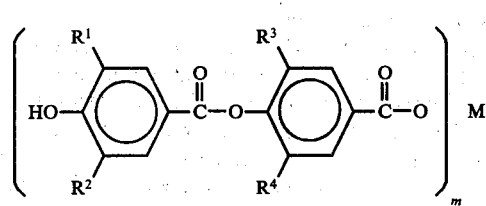

wherein
$R^1$ and $R^2$ are (lower)alkyl or (lower)cycloalkyl groups,
$R^3$ and $R^4$ are hydrogen, (lower)alkyl or (lower)cycloalkyl,
M is metal or an alkyl metal moiety, said metal having a valency of 1 to 4, and
$m$ is an integer from 1 to 4.

4. A composition of claim 3 which additionally contains a phenolic antioxidant.

5. A composition of claim 3 wherein the organic material is a polyolefin.

6. A composition of claim 3 wherein the organic material is polypropylene.

7. A composition of claim 3 wherein additionally contains a phenolic antioxidant selected from the group consisting of n-octadecyl β-(3,5-di-t-butyl-4-hydroxyphenyl) propionate, pentaerythriol tetrakis-[3-(3,5-di-t-butyl-4-hydroxyphenyl)propionate], and dioctadecyl-3,5-di-t-butyl-4-hydroxybenzylphosphonate.

8. A composition of claim 3 wherein the benzoyloxybenzoate is selected from the group consisting of nickel-bis-[4-(3,5-di-tert-butyl-4-hydroxybenzoyl)-3,5-di-tert-butylbenzoate]; cupric-bis-[4-(3,5-di-tert-butyl-4-hydroxybenzoyloxy)-3,5-di-tert-butylbenzoate]; zinc-bis-[4-(3,5-di-tert-butyl-4-hydroxybenzoyloxy)-3,5-di-tert-butylbenzoate]; manganese-bis-[4-(3,5-di-tert-butyl-4-hydroxybenzoyloxy)-3,5-di-tert-butylbenzoate]; ferric-tris-[4-(3,5-di-tert-butyl-4-hydroxybenzoyloxy)-3,5-di-tert-butylbenzoate]; and di-n-butyltin-bis-[4-(3,5-di-t-butyl-4-hydroxybenzoyloxy)-3,5-di-tert-butylbenzoate].

9. A composition of claim 3 wherein the benzoyloxybenzoate is nickel-bis-[4-(3,5-di-tert-butyl-4-hydroxybenzoyloxy)-3,5-di-tert-butylbenzoate].

10. A composition of claim 6 in which the benzoyloxybenzoate is nickel-bis-[4-(3,5-di-tert-butyl-4-hydroxybenzoyloxy)-3,5-di-tert-butylbenzoate] and which additionally contains a phenolic antioxidant.

11. A composition of claim 10 wherein the phenolic antioxidant is dioctadecyl 3,5-di-t-butyl-4-hydroxybenzylphosphonate.

12. A composition of claim 11 which additionally contains 2-(2'-hydroxy-3',5'-di-t-butylphenyl)-5-chloro-1,2,3-benzotriazole.

* * * * *